United States Patent [19]

Barnes et al.

[11] 4,387,098
[45] Jun. 7, 1983

[54] IMIDAZO[1,2-A]QUINOLINE DERIVATIVES USEFUL AS ANXIOLYTICS

[75] Inventors: Alan C. Barnes, Cirencester; Peter A. Robson, Upper Stratton, both of England

[73] Assignee: Roussel Uclaf, Paris, France

[21] Appl. No.: 361,779

[22] Filed: Mar. 25, 1982

[30] Foreign Application Priority Data

Apr. 3, 1981 [GB] United Kingdom ............... 81-10586

[51] Int. Cl.³ ..................... A61K 31/47; C07D 471/14
[52] U.S. Cl. ...................................... 424/256; 546/84; 546/153; 546/174; 546/86; 546/87; 546/85
[58] Field of Search ........................... 546/84; 424/258

[56] References Cited

U.S. PATENT DOCUMENTS 4,279,912 7/1981 Ager et al. ........................... 424/258

Primary Examiner—John M. Ford
Assistant Examiner—Bernard Dentz
Attorney, Agent, or Firm—Hammond & Littell, Weissenberger and Muserlian

[57] ABSTRACT

Novel imidazo[1,2-a]quinolines of the formula

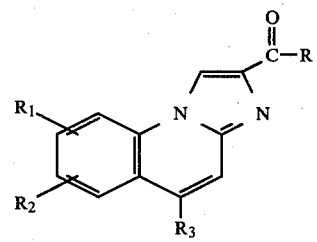

wherein R is selected from the group consisting of alkyl of 1 to 8 carbon atoms, thienyl, pyridyl and phenyl optionally substituted with at least one member of the group consisting of halogen, alkyl of 1 to 5 carbon atoms and alkoxy of 1 to 5 carbon atoms, $R_1$ and $R_2$ are individually selected from the group consisting of hydrogen, halogen, alkyl and alkoxy of 1 to 8 carbon atoms,s cyclohexyl, —$NO_2$ and phenoxy, $R_3$ is selected from the group consisting of alkoxy and alkylthio of 1 to 8 carbon atoms and their non-toxic, pharmaceutically acceptable acid addition salts having a remarkable anxiolytic activity and a hypnotic activity and their preparation.

21 Claims, No Drawings

IMIDAZO[1,2-A]QUINOLINE DERIVATIVES USEFUL AS ANXIOLYTICS

STATE OF THE ART

Commonly assigned U.S. Pat. No. 4,145,419, No. 4,279,912, No. 4,151,280, No. 4,207,318 and No. 4,254,123 and U.S. patent application Ser. No. 118,445 filed Feb. 4, 1980, now U.S. Pat. No. 4,333,934 all describe tricyclic compounds of this nature with fundamentally different pharmacological properties.

OBJECTS OF THE INVENTION

It is an object of the invention to provide the novel imidazo[1,2-a]quinolines of formula I and their non-toxic, pharmaceutically acceptable acid addition salts and a process for their preparation.

It is another object of the invention to provide novel anxiolytic compositions and a novel method of inducing anxiolytic activity in warm-blooded animals.

These and other objects and advantages of the invention will become obvious from the following detailed description.

THE INVENTION

The novel compounds of the invention are selected from the group consisting of imidazo[1,2-a]quinolines of the formula

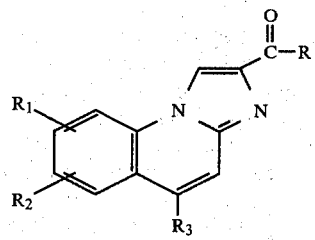

wherein R is selected from the group consisting of alkyl of 1 to 8 carbon atoms, thienyl, pyridyl and phenyl optionally substituted with at least one member of the group consisting of halogen, alkyl of 1 to 5 carbon atoms and alkoxy of 1 to 5 carbon atoms, $R_1$ and $R_2$ are individually selected from the group consisting of hydrogen, halogen, alkyl and alkoxy of 1 to 8 carbon atoms, cyclohexyl, —$NO_2$ and phenoxy, $R_3$ is selected from the group consisting of alkoxy and alkylthio of 1 to 8 carbon atoms and their non-toxic, pharmaceutically acceptable acid addition salts. When R, $R_1$ or $R_2$ are alkyl or alkoxy, they preferably contain 1 to 5 carbon atoms.

Examples of R, $R_1$ and/or $R_2$ as alkyl are methyl, ethyl, propyl, isopropyl, butyl, pentyl and octyl and as alkoxy are methoxy, ethoxy, propoxy, isopropoxy, butoxy, isobutoxy and octyloxy. Examples of $R_3$ as alkylthio are methylthio, ethylthio and propylthio. When $R_1$ and/or $R_2$ are halogen, they are preferably fluorine, chlorine or bromine. R may also be phenyl substituted with bromine, chlorine, methyl or methoxy, preferably in the para-position.

Examples of suitable acids for the formation of the non-toxic, pharmaceutically acceptable acid addition salts are mineral acids such as hydrochloric acid, hydrobromic acid, hydroiodic acid, nitric acid, sulfuric acid or phosphoric acid and organic acids such as formic acid, acetic acid, propionic acid, benzoic acid, maleic acid, fumaric acid, succinic acid, tartaric acid, citric acid, oxalic acid, glyoxylic acid, aspartic acid, alkane sulfonic acids such as methanesulfonic acid and arylsulfonic acids such as benzenesulfonic acid.

Among the preferred compounds of formula I are those wherein R is methyl or phenyl, those wherein $R_1$ and $R_2$ are individually hydrogen, chlorine, methyl, ethyl or methoxy and their non-toxic, pharmaceutically acceptable acid addition salts. Especially preferred are those wherein R is phenyl and $R_1$ is hydrogen, $R_2$ is hydrogen or alkyl of 1 to 5 carbon atoms and $R_3$ is alkoxy of 1 to 5 carbon atoms.

Specific preferred compounds of formula I are (7-ethyl-5-methoxy-imidazo[1,2-a]quinolin-2-yl)-phenyl-methanone and the mesylate thereof, (5-methoxy-imidazo[1,2-a]quinolin-2-yl)-phenyl-methanone, (5-isopropoxy-imidazo[1,2-a]quinolin-2-yl)-phenyl-methanone and (5-methylthio-imidazo[1,2-a]quinolin-2-yl)-phenyl-methanone and their non-toxic, pharmaceutically acceptable acid addition salts.

A process of the invention (method A) for the preparation of the compounds of formula I comprises reacting a compound of the formula

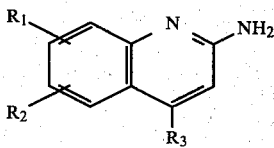

wherein $R_1$, $R_2$ and $R_3$ are as defined above with a compound of the formula $$X—CH_2—CO—CO—R \qquad III$$

wherein X is a group capable of elimination to form the anion $X^-$ such as a halogen e.g. bromine, and R is as defined above and cyclizing the obtained compound of the formula

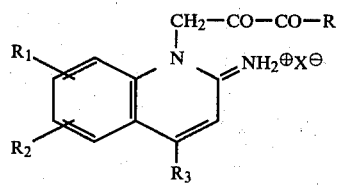

wherein R, $R_1$, $R_2$, $R_3$ and $X^-$ have the above definitions to obtain the corresponding compound of formula I.

Preferably, the compound of formula IV is prepared in situ and cyclized as described above without separate isolation. The reaction of the compound of formula II with the compound of formula III is preferably effected in the presence of an organic solvent such as, for example, dimethoxymethane. Cyclization may, for example, be effected by heating the compound of formula IV in the presence of an organic solvent e.g. to the boiling point of the reaction mixture. Suitable organic solvents include, for example, alkanols such as ethanol.

Generally, the above cyclization reaction leads to the formation of an acid addition salt of the compound of formula I i.e. with the acid HX and the free base of formula I may be obtained therefrom, if desired without previous isolation, by treatment with a base such as an alkali metal hydroxide or carbonate like potassium carbonate. The base of formula I may be converted into other acid addition salts by reaction with the appropriate acid, preferably in a stoichiometric amount, according to conventional methods.

The compounds of formula II when they are not known, may be prepared in an analogous way to the process described in our U.S. Pat. No. 4,279,912 or in British Pat. No. 1,542,778. The compounds of formula II may also be prepared as described in J. Chem. Soc., 1958, p. 614 et seq. or in Synthesis, 1977, p. 500. The compounds of formula III in which R is phenyl may be prepared as described in Hel. Chim. Acta, 1946., Vol. 29, 1247. Compounds of formula III in which R is methyl may be prepared as described in U.S. Pat. No. 2,821,555 and the remaining compounds of formula III wherein R is alkyl of 2 to 5 carbon atoms may be prepared by a method analogous thereto.

An alternative process of the invention (method B) for the preparation of compounds of formula I having the formula

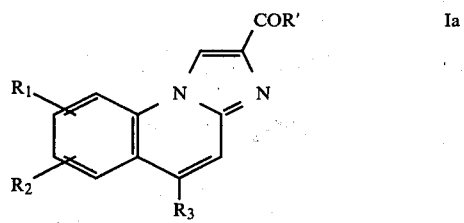

Ia wherein $R_1$, $R_2$ and $R_3$ have the above definitions and R' is phenyl optionally substituted with at least one member of the group consisting of halogen, alkyl of 1 to 5 carbon atoms, alkoxy of 1 to 5 carbon atoms, thienyl and pyridyl and the acid addition salts thereof comprises reacting a compound of the formula

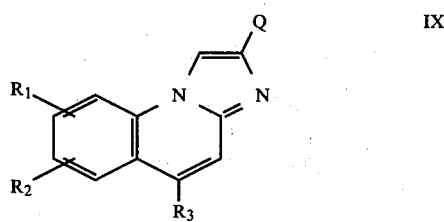

IX wherein $R_1$, $R_2$ and $R_3$ have the above definitions and Q is an esterified carboxyl group, e.g. an alkoxycarbonyl or aralkoxycarbonyl group, preferably an alkoxycarbonyl group in which the alkoxy moiety contains 1 to 3 carbon atoms with a reducing agent to obtain a compound of the formula

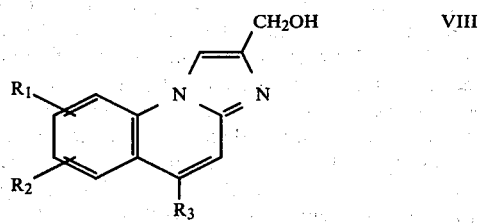

VIII wherein $R_1$, $R_2$ and $R_3$ have the above definitions, oxidizing the latter to obtain a compound of the formula

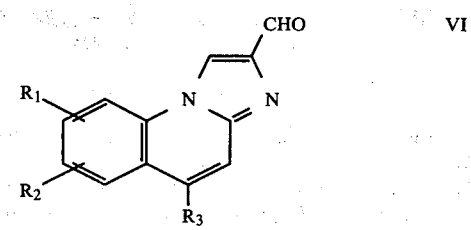

VI wherein $R_1$, $R_2$ and $R_3$ have the above-definitions, reacting the said compound with a Grignard reagent formed from a compound

R'—Y    VII wherein R' is as defined above, and Y is chlorine, bromine or iodine, preferably a bromine to obtain a compound of the formula

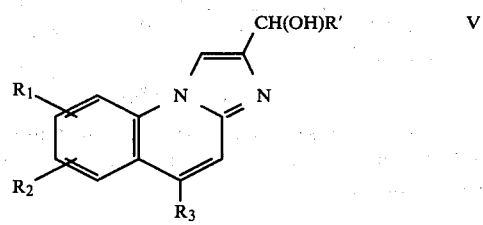

V wherein $R_1$, $R_2$, $R_3$ and R' are as defined above and then reacting the latter with an oxidizing agent to obtain the compound of formula Ia, and, if desired, converting the compound of formula Ia into its acid addition salts.

The reduction of the compounds of formula IX is effected with conventional reducing agents and the use of lithium aluminum hydride is preferred but other reducing agents may be used such as sodium borohydride, aluminum chloride and lithium borohydride. The oxidation of the compounds of formula VIII may be performed using conventional oxidizing agents such as manganese dioxide or with nitric acid, ferric chloride and chromic oxide/pyridine. The oxidation may alternatively be effected with an Oppenauer oxidation or by dehydrogenation over a copper catalyst.

The reaction between the compounds of formulae VI and VII may be performed under anhydrous conditions in a suitable organic solvent, preferably tetrahydrofuran. Oxidation of the compound of formula V may be performed using conventional oxidizing agents. The use of manganese dioxide is preferred but other agents such as described above may be used.

The starting materials of formula IX may generally be prepared by the method disclosed in British Pat. No. 1,596,652 or by analogous methods.

If desired, a compound of formula Ia obtained by method B may subsequently be converted into an acid addition salt thereof.

The novel anxiolytic compositions of the invention are comprised of an anxiolytically effective amount of at least one compound of formula I and their non-toxic, pharmaceutically acceptable acid addition salts and an inert pharmaceutical carrier or excipient. The compositions may contain other active ingredients and may be in the form of tablets, dragees, capsules, granules, ampoules, suppositories and injectable solutions or suspensions.

The compositions of the invention due to their remarkable anxiolytic activity and a certain hypnotic activity are thus useful in the treatment of anxiety, chronic anxiety accompanied by agitation, irritability and aggression, anxiety accompanied by insomnia and muscular tension and distress.

Examples of suitable excipients are lactose, starch, magnesium stearate, cocoa butter, aqueous or non-aqueous vehicles, fatty substances of animal or vegetable origin, paraffin derivatives, glycols, various wetting, dispersing or emulsifying agents and/or preservatives.

Advantageously the compositions may be formulated as dosage units, each unit being adapted to supply a fixed dose of active ingredient. Suitable dosage units for adults contain from 0.1 mg to 100 mg, preferably from 0.1 mg to 20 mg of active ingredient. The oral daily dosage, which may be varied according to the compound used, the subject treated and the complaint concerned, may, for example, be from 0.5 to 200 mg per day in adults.

The novel method of the invention for inducing anxiolytic activity in warm-blooded animals, including humans, comprises administrating to warm-blooded animals an anxiolytially effective amount of least one compound of formula I and their non-toxic, pharnaceutically acceptable acid addition salts. The compounds may be administered orally, rectally or parenterally.

The novel intermediate compounds of the invention are the compounds of formula IV and their non-toxic, pharmaceutically acceptable acid addition salts and the compounds of formulae V, VI and VIII which have the general formula

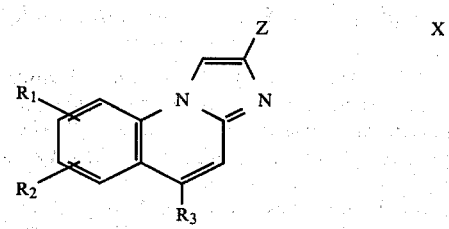

wherein $R_1$, $R_2$ and $R_3$ are as defined above and Z is —CHO or group —CH(OH)R" where R" is hydrogen or R' as defined above.

In the following examples thereof are described several preferred embodiments to illustrate the invention. However, it should be understood that the invention is not intended to be limited to the specific embodiments.

EXAMPLE 1

(Method A)

7-Ethyl-5-methoxy-imidazo[1,2-a]quinolin-2-yl)-phenylmethanone 112.5 g of 3-bromo-1-phenyl-propan-1,2-dione were added to a mixture of 90 g of 2-amino-6-ethyl-4-methoxy-quinoline and 1.5 liters of dimethoxymethane and the mixture was stirred at room temperature for 2.5 hours and was filtered to remove 6-ethyl-4-methoxy-[1-(3'-phenyl-2',3'-dioxopropyl)-]-quinolin-2-iminium hydrobromide. The latter was washed with ether and was suspended in 1.25 liters of ethanol. The suspension was refluxed until a clear solution was obtained and the solution was cooled to room temperature and was filtered to obtain 75 g of product. The filtrate was concentrated under reduced pressure and was diluted with ether to obtain 30 g of product. The combined products were shaken with a mixture of chloroform and aqueous potassium carbonate and the organic phase was washed with water, dried over magnesium sulfate and evaporated under reduced pressure. Ethanol was added to the mixture to obtain in 2 crops of 54.7 g of 7-ethyl-5-methoxy-imidazo[1,2-a]quinolin-2-yl)-phenylmethanone in the form of pale yellow crystals melting at 196°–198° C.

NMR Spectrum (CDCl$_3$): 1.44 (s 1H; 1-H).

EXAMPLES 2 TO 10

Using the procedure of Example 1, the appropriate quinoline and propane-1,2-dione were reacted to obtain the compounds of Tables I and II with the NMR Spectrum (deuterochloroform) having a peak in the range of 1.2–1.7 (s,1H; 1-H).

TABLE I

| Example | R | $R_1$ | $R_2$ | $R_3$ | Form | % Yield | Melting Point °C. | IR Spectrum (KBr disc) cm$^{-1}$ |
|---|---|---|---|---|---|---|---|---|
| 1 | —⟨⟩ | H | 7-C$_2$H$_5$ | OCH$_3$ | — | 37 | 196–8 | 3140,1645,1606 |
| 2 | —⟨⟩ | H | H | SCH$_3$ | — | 25 | 209 | 3125,1645,1602 |
| 3 | —⟨⟩ | 8-OCH$_3$ | H | OCH$_3$ | — | 16 | 180–2 | 1640 |
| 4 | —⟨⟩ | H | H | OCH$_3$ | — | 12 | 190–1 | 3140,1650 |
| 5 | —⟨⟩ | H | 7-C$_2$H$_5$ | OCH$_3$ | CH$_3$SO$_3$H | | 228–30 | 3075,1665,1644,1601 |
| 6 | —CH$_3$ | H | 7-C$_2$H$_5$ | OCH$_3$ | — | 30 | 148 | 3140,1690 |
| 7 | —⟨⟩ | H | 7-Cl | OCH$_3$ | — | 12 | 228–34 | 3140,1650 |

TABLE I-continued

| Example | R | $R_1$ | $R_2$ | $R_3$ | Form | % Yield | Melting Point °C. | IR Spectrum (KBr disc) cm$^{-1}$ |
|---|---|---|---|---|---|---|---|---|
| 8 |  | H | H | OiPr | — | 6 | 162 | 3140,3000,2900,1640 |
| 9 |  | H | H | OC$_2$H$_5$ | — | 14 | 210 | 3140,1640 |
| 10 |  | H | H | OBu | — | 20 | 159 | 3360,3090,2980, 1640,1620 |

TABLE 2

| Example | Formula | Molecular Weight | Theory/found % C | % H | % N | % X |
|---|---|---|---|---|---|---|
| 1 | C$_{21}$H$_{18}$N$_2$O$_2$ | 330.37 | 76.33 76.5 | 5.50 5.5 | 8.48 8.5 | |
| 2 | C$_{19}$H$_{14}$N$_2$OS | 318.39 | 71.67 71.8 | 4.43 4.5 | 8.80 8.8 | |
| 3 | C$_{20}$H$_{16}$N$_2$O$_3$ | 332.36 | 72.28 72.2 | 4.85 4.9 | 8.43 8.4 | |
| 4 | C$_{19}$H$_{14}$N$_2$O$_2$ | 302.33 | 75.48 75.3 | 4.67 4.7 | 9.26 9.2 | |
| 5 | C$_{22}$H$_{22}$N$_2$O$_5$S | 426.49 | 61.95 62.2 | 5.20 5.2 | 6.57 6.7 | 7.51(S) 7.7 |
| 6 | C$_{16}$H$_{16}$N$_2$O$_2$ | 268.31 | 71.62 71.7 | 6.01 6.1 | 10.44 10.6 | |
| 7 | C$_{19}$H$_{13}$ClN$_2$O$_3$ | 336.7 | 67.76 67.5 | 3.89 4.0 | 8.32 8.4 | 10.53(Cl) 10.7 |
| 8 | C$_{21}$H$_{18}$N$_2$O$_2$ | 330.36 | 76.35 76.4 | 5.49 5.6 | 8.48 8.4 | |
| 9 | C$_{20}$H$_{16}$N$_2$O$_2$ | 316.34 | 75.93 75.9 | 5.10 5.2 | 8.85 8.8 | |
| 10 | C$_{22}$H$_{20}$N$_2$O$_2$ | 344.39 | 76.72 76.5 | 5.85 5.9 | 8.13 8.1 | |

EXAMPLE 11

(Method B)

(4-ethyl-phenyl)(5-methoxy-imidazo[1,2-a]quinolin-2-yl)-methanone

STEP A:

5-methoxy-imidazo[1,2-a]quinoline-2-methanol

A suspension of 19.71 g (73 mmol) of ethyl 5-methoxyimidazo[1,2-a]quinoline-2-carboxylate in 350 ml of freshly distilled anhydrous tetrahydrofuran was stirred under a nitrogen atmosphere at room temperature and 3.33 g (88 mmol) of lithium aluminum hydride were added thereto in portions over 3 hours. The mixture was stirred for 4 hours and excess hydride was destroyed by dropwise addition of wet tetrahydrofuran followed by water. The mixture was poured into 1.5 liters of water and the mixture was extracted with 500 ml of a chloroform-methanol mixture. The mixture was filtered through a celite pad and the aqueous phase was extracted again with a chloroform-methanol mixture. The combined organic phases were dried over anhydrous magnesium sulfate and evaporated to dryness under reduced pressure. The residue was triturated with ethyl acetate, filtered, washed with ethyl acetate and dried under reduced pressure over P$_2$O$_5$ to obtain 14.87 g (89% yield) of 5-methoxy-imidazo[1,2-a]quinoline-2-methanol as a white crystalline solid melting at 173°–175° C.

STEP B:

5-methoxy-imidazo[1,2-a]quinolin-2-carboxaldehyde

A solution of 14.6 g (64 mmol) of the product of Step A in 700 ml of chloroform was vigorously stirred while 60 g of activated manganese dioxide were added thereto and the mixture was then stirred at room temperature for 28 hours. The mixture was filtered and the filter was throughly washed with chloroform. The filtrate was evaporated to dryness under reduced pressure and the residue was crystallized from ethyl acetate to obtain 10.9 g (75% yield) of 5-methoxyimidazo[1,2-a]quinolin-2-carboxaldehyde in the form of a white crystalline solid melting at 195°–196° C.

STEP C:

(4-ethyl-phenyl)(5-methoxy-imidazo[1,2-a]quinoline-2-yl)-methanol 2.78 g (15 mmol) of p-bromo-ethylbenzene were added dropwise to a stirred suspension of 0.36 g (15 mg-atoms) of magnesium turnings in 25 ml of anhydrous tetrahydrofuran containing an iodine crystal to form a Grignard reagent and the resulting solution was added dropwise to a suspension of 2.26 g (10 mmol) of the product of Step B in 50 ml of anhydrous tetrahydrofuran. The mixture was stirred at room temperature for one hour and was poured into 200 ml of water. The mixture was extracted with 200 ml of chloroform and was filtered through a celite pad. The separated aqueous phase was extracted twice with 100 ml of chloroform and the combined organic phases were dried over anhydrous magnesium sulfate and evaporated to dryness under reduced pressure to obtain a green gum. The latter was chromatographed over 200 g of silica gel and was eluted with a 95-5 chloroform-methanol mixture to obtain 2.12 g (64% yield) of (4-ethyl-phenyl)(5-methoxy-imidazo[1,2-a]quinolin-2-yl)-methanol in the form of a green gum.

STEP D:

(4-ethyl-phenyl)(5-methoxy-imidazo[1,2-a]quinolin-2-yl)-methanone 8 g of activated manganese dioxide were added to a solution of 1.99 g (6 mmol) of the product of Step C in 100 ml of chloroform and the mixture was vigorously stirred at room temperature for 16 hours and was filtered. The filter was washed with chloroform and the filtrate was evaporated to dryness under reduced pressure. The residue was crystallized from ethyl acetate to obtain 1.32 g (67% yield) of (4-ethylphenyl)(5-methoxy-imidazo[1,2-a]quinolin-2-yl)-methanone in the form of a light yellow crystalline solid melting at 147°–148° C. Overall yield based on the starting ester was 29%.

Analysis: $C_{21}H_{18}N_2O_2$; molecular weight=330.38
Calculated: %C: 76.34; %H: 5.49; %N: 8.48; Found: %C: 76.3; %H: 5.6; %N: 8.5.

IR Spectrum (KBr disc):
Absorption at 3130, 1630 and 1600 cm$^{-1}$

EXAMPLES 12 TO 33

The products set forth in Tables III and IV were prepared by Method A or B as indicated in the Tables.

TABLE III

| Ex | R | $R_1$ | $R_2$ | $R_3$ | Yield % | Method | Melting Point °C. | IR Spectrum (KBr disc) cm$^1$ |
|---|---|---|---|---|---|---|---|---|
| 12 |  | H | H | OPr | 13 | A | 179 | 3120,1640 |
| 13 |  | H | 7-$CH_3$ | $OCH_3$ | 30 | A | 218–20 | 3120,1630,1600 |
| 14 |  | H | 7-$OCH_3$ | $OCH_3$ | 20 | A | 233–5 | 3130,1640,1600 |
| 15 |  | H | 7-iPr | $OCH_3$ | 23 | A | 187–8 | 3110,1630 |
| 16 |  | H | 7-Bu | $OCH_3$ | 26 | A | 165–7 | 3120,1630 |
| 17 | 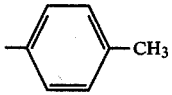 | H | H | $OCH_3$ | 35 | B | 213–3 | 3120,1630,1600 |
| 18 | 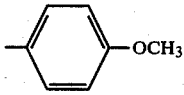 | H | H | $OCH_3$ | 31 | B | 170–1 | 3120,1630,1600 |
| 19 |  | 9-$OCH_3$ | H | $OCH_3$ | 24.5 | A | 189–91 | 3180,1640 |
| 20 | 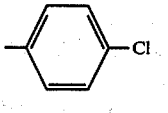 | H | H | $OCH_3$ | 25 | B | 245–6 | 3130,1635,1585 |
| 21 |  | H | H | $OCH_3$ | 36 | B | 257–9 | 3100,1630,1610 |
| 22 |  | 8-Cl | H | $OCH_3$ | 30 | A | 211.13 | 3100,1640,1600 |
| 23 |  | 9-Cl | H | $OCH_3$ | 43 | A | 149–50 | 3200,1630,1600 |

TABLE III-continued

| Ex | R | R₁ | R₂ | R₃ | Yield % | Method | Melting Point °C. | IR Spectrum (KBr disc) cm$^{-1}$ |
|---|---|---|---|---|---|---|---|---|
| 24 |  | 8-CH₃ | H | OCH₃ | 21.6 | A | 192-3 | 3130,1640,1600 |
| 25 |  | H | 6-CH₃ | OCH₃ | 9.4 | A | 209-10 | 3130,1640,1600 |
| 26 |  | H | 7-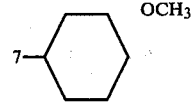 | OCH₃ | 70 | A | 227 | 3120,1640 |
| 27 |  | H | 7-OPh | OCH₃ |  | A | 210-12 | 3120,1640 |
| 28 |  | H | 7-C₂H₅ | OCH₃ | 13 | B | 172-3 | 3120,1635,1600 |
| 29 |  | H | 7-C₂H₅ | OCH₃ | 24 | B | 170-1 | 3120,1640,1605 |
| 30 |  | H | 7-C₂H₅ | OCH₃ | 15 | B | 185-6 | 3180,1650,1630 |
| 31 |  | H | 7-F | OCH₃ | 19 | A | 234-5 | 3160,1630,1600 |
| 32 |  | H | 7-nPr | OCH₃ | 30 | A | 185-6 | 3120,1640,1600 |
| 33 |  | 8-CH₃ | 7-CH₃ | OCH₃ | 28 | A | 244-5 | 3120,1630,1590 |

TABLE IV

| Ex | Formula | Molecular Weight | Analysis Theory/Found | | | |
|---|---|---|---|---|---|---|
| | | | % C | % H | % N | % X |
| 12 | C₂₁H₁₈N₂O₂ | 330-38 | 76.34 | 5.49 | 8.48 | |
| | | | 76.4 | 5.6 | 8.5 | |
| 13 | C₂₀H₁₆N₂O₂ | 316.36 | 75.93 | 5.10 | 8.85 | |
| | | | 75.6 | 5.2 | 8.8 | |
| 14 | C₂₀H₁₆N₂O₃ | 332.36 | 72.28 | 4.85 | 8.43 | |
| | | | 72.5 | 4.9 | 8.4 | |
| 15 | C₂₂H₂₀N₂O₂ | 344.39 | 76.72 | 5.85 | 8.13 | |
| | | | 76.9 | 5.9 | 8.2 | |
| 16 | C₂₃H₂₂N₂O₂ | 358.45 | 77.07 | 6.19 | 7.81 | |
| | | | 77.3 | 6.2 | 7.8 | |
| 17 | C₂₀H₁₆N₂O₂ | 316.36 | 75.93 | 5.10 | 8.85 | |
| | | | 75.9 | 5.15 | 8.8 | |
| 18 | C₂₀H₁₆N₂O₃ | 332.36 | 72.28 | 4.85 | 8.43 | |
| | | | 72.2 | 4.9 | 8.4 | |
| 19 | C₂₀H₁₆N₂O₃ | 332.36 | 72.28 | 4.85 | 8.43 | |
| | | | 72.1 | 4.9 | 8.4 | |
| 20 | C₁₉H₁₃ClN₂O₂ | 336.77 | 67.76 | 3.89 | 8.32 | 10.53(Cl) |
| | | | 67.75 | 4.0 | 8.3 | 10.8 |
| 21 | C₁₇H₁₂N₂O₂S | 308.36 | 66.22 | 3.92 | 9.08 | 10.40(S) |
| | | | 66.2 | 4.0 | 9.1 | 10.4 |
| 22 | C₁₉H₁₃ClN₂O₂ | 336.77 | 67.76 | 3.89 | 8.32 | 10.53(Cl) |
| | | | 67.8 | 3.95 | 8.3 | 10.6 |

TABLE IV-continued

| Ex | Formula | Molecular Weight | Analysis Theory/Found | | | |
|---|---|---|---|---|---|---|
| | | | % C | % H | % N | % X |
| 23 | $C_{19}H_{13}ClN_2O_2$ | 336.77 | 67.76 | 3.89 | 8.32 | 10.53(Cl) |
| | | | 67.8 | 3.9 | 8.3 | 10.6 |
| 24 | $C_{20}H_{16}N_2O_2$ | 316.36 | 75.93 | 5.10 | 8.85 | |
| | | | 75.7 | 5.2 | 8.9 | |
| 25 | $C_{20}H_{16}N_2O_2$ | 316.34 | 75.93 | 5.10 | 8.85 | |
| | | | 75.65 | 5.2 | 8.9 | |
| 26 | $C_{25}H_{24}N_2O_2$ | 384.45 | 78.10 | 6.29 | 7.29 | |
| | | | 78.2 | 6.4 | 7.3 | |
| 27 | $C_{25}H_{18}N_2O_3$ | 394.43 | 76.13 | 4.60 | 7.10 | |
| | | | 75.9 | 4.7 | 7.0 | |
| 28 | $C_{22}H_{29}N_2O_3$ | 360.42 | 73.32 | 5.59 | 7.77 | |
| | | | 73.3 | 5.65 | 7.8 | |
| 29 | $C_{23}H_{22}N_2O_2$ | 358.45 | 77.07 | 6.19 | 7.82 | |
| | | | 77.3 | 6.2 | 7.9 | |
| 30 | $C_{20}H_{17}N_3O_2$ | 331.38 | 72.49 | 5.17 | 12.68 | |
| | | | 72.6 | 5.2 | 12.8 | |
| 31 | $C_{19}H_{13}N_2O_2F$ | 320.32 | 71.24 | 4.09 | 8.74 | 5.93(F) |
| | | | 71.1 | 4.1 | 8.7 | 5.8 |
| 32 | $C_{22}H_{20}N_2O_2$ | 344.39 | 76.72 | 5.85 | 8.13 | |
| | | | 76.8 | 5.9 | 8.2 | |
| 33 | $C_{21}H_{18}N_2O_2$ | 330.40 | 76.34 | 5.49 | 8.48 | |
| | | | 76.2 | 5.55 | 8.4 | |

EXAMPLE 34

Tablets were prepared containing 20 mg of (7-ethyl-5-methoxy-imidazo[1,2-a]quinolin-2-yl)-phenyl-methanone or of (5-methoxy-imidazo[1,2-a]quinolin-2-yl)-phenyl-methanone and sufficient excipient of lactose, starch, talc and magnesium stearate for a final tablet weight of 150 mg.

PHARMACOLOGICAL DATA

A. The affinity of the compounds for the benzodiazepine receptor was assessed using the radioligand [$^3$H] flunitrazepam and modifications of the original radio receptor binding method of Squires and Braestrup (Nature, 1977, Vol. 266, p. 732). The values of Table V are nanomolar concentrations of test compound which inhibited the specific binding of 0.6 nM[$^3$H] flunitrazepam to rat forebrain membrane preparations by 50% (IC$_{50}$nM).

TABLE V

| Product of Example | IC$_{50}$ nM |
|---|---|
| 1 | 14 |
| 2 | 500 |
| 3 | 5000 |
| 4 | 27 |
| 5 | — |
| 6 | 1300 |
| 7 | 600 |
| 8 | 470 |
| 9 | 540 |
| 10 | 1000 |
| 11 | 67 |
| 12 | 1000 |
| 13 | 21 |
| 14 | 51 |
| 15 | 25 |
| 16 | 57 |
| 17 | 19 |
| 18 | 37 |
| 19 | 630 |
| 20 | 96 |
| 21 | 24 |
| 22 | 340 |
| 23 | 132 |
| 24 | 290 |
| 25 | 11 |
| 26 | 10000 |

TABLE V-continued

| Product of Example | IC$_{50}$ nM |
|---|---|
| 27 | 210 |
| 28 | 30 |
| 29 | 51 |
| 30 | 92 |
| 31 | 74 |
| 32 | — |
| 33 | — |

B. Screening for anxiolytic activity was carried out by the one-day lick shock method of Vogel et al [Psychopharmacologia, 1971 Vol. 21, p. 1]. The values of Table VI are the minimum effective doses (MED) in mg/kg orally at which there was an observed increase in shocks above control.

TABLE VI

| Product of Example | MED mg/kg |
|---|---|
| 1 | 20 |
| 4 | 25 |
| 6 | 20 |
| 13 | 25 |
| 15 | 10 |
| 16 | 25 |

Various modifications of the products and processes of the invention may be made without departing from the spirit or scope thereof and it is to be understood that the invention is intended to be limited only as defined in the appended claims.

What is claimed is:

1. A compound selected from the group consisting of imidazo[1,2-a]quinolines of the formula

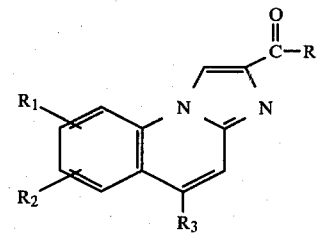

wherein R is selected from the group consisting of alkyl of 1 to 8 carbon atoms, thienyl, pyridyl and phenyl optionally substituted with at least one member of the group consisting of halogen, alkyl of 1 to 5 carbon atoms and alkoxy of 1 to 5 carbon atoms, $R_1$ and $R_2$ are individually selected from the group consisting of hydrogen, halogen, alkyl and alkoxy of 1 to 8 carbon atoms, cyclohexyl, —$NO_2$ and phenoxy, $R_3$ is selected from the group consisting of alkoxy and alkylthio of 1 to 8 carbon atoms and their non-toxic, pharmaceutically acceptable acid addition salts.

2. A compound of claim 1 wherein R is selected from the group consisting of methyl and phenyl and $R_1$ and $R_2$ are individually selected from the group consisting of hydrogen, chlorine, methyl, ethyl and methoxy.

3. A compound of claim 1 wherein R is phenyl, $R_1$ is hydrogen, $R_3$ is alkoxy of 1 to 5 carbon atoms and $R_2$ is selected from the group consisting of hydrogen and alkyl of 1 to 5 carbon atoms.

4. A compound of claim 1 selected from the group consisting of (7-ethyl-5-methoxyimidazo[1,2-a]quinolin-2-yl)-phenylmethanone and its mesylate.

5. A compound of claim 1 selected from the group consisting of (5-methoxyimidazo[1,2-a]quinolin-2-yl)-phenylmethanone and its non-toxic, pharmaceutically acceptable acid addition salts.

6. A compound of claim 1 selected from the group consisting of (5-isopropoxyimidazo[1,2-a]quinolin-2-yl)-phenyl methanone and its non-toxic, pharmaceutically acceptable acid addition salts.

7. A compound of claim 1 selected from the group consisting of (5-methylthioimidazo[1,2-a]quinolin-2-yl-phenylmethanone and its non-toxic, pharmaceutically acceptable acid addition salts.

8. An anxiolytic composition comprising an anxiolytically effective amount of at least one compound of claim 1 and an inert pharmaceutical carrier.

9. A composition of claim 8 wherein R is selected from the group consisting of methyl and phenyl and $R_1$ and $R_2$ are individually selected from the group consisting of hydrogen, chlorine, methyl, ethyl and methoxy.

10. A composition of claim 8 wherein R is phenyl, $R_1$ is hydrogen, $R_3$ is alkoxy of 1 to 5 carbon atoms and $R_2$ is selected from the group consisting of hydrogen and alkyl of 1 to 5 carbon atoms.

11. A composition of claim 8 wherein the active compound is selected from the group consisting of (7-ethyl-5-methoxyimidazo[1,2-a]quinolin-2-yl)-phenylmethanone and its mesylate.

12. A composition of claim 8 wherein the active compound is selected from the group consisting of (5-methoxyimidazo[1,2-a]quinolin-2-yl)-phenylmethanone and its non-toxic, pharmaceutically acceptable acid addition salts.

13. A composition of claim 8 wherein the active compound is selected from the group consisting of (5-isopropoxyimidazo[1,2-a]quinolin-2-yl)phenyl-methanone and its non-toxic, pharmaceutically acceptable acid addition salts.

14. A composition of claim 8 wherein the active compound is selected from the group consisting of (5-methylthioimidazo[1,2-a]quinolin-2-yl)-phenyl-methanone and its non-toxic, pharmaceutically acceptable acid addition salts.

15. A method of inducing anxiolytic activity in warm-blooded animals comprising administering to warm-blooded animals an anxiolytically effective amount of at least one compound of claim 1.

16. A method of claim 15 wherein R is selected from the group consisting of methyl and phenyl and $R_1$ and $R_2$ are individually selected from the group consisting of hydrogen, chlorine, methyl, ethyl and methoxy.

17. A method of claim 15 wherein R is phenyl, $R_1$ is hydrogen, $R_3$ is alkoxy of 1 to 5 carbon atoms and $R_2$ is selected from the group consisting of hydrogen and alkyl of 1 to 5 carbon atoms.

18. A method of claim 15 selected from the group consisting of (7-ethyl-5-methoxyimidazo[1,2-a]quinolin-2-yl)-phenylmethanone and its mesylate.

19. A method of claim 15 selected from the group consisting of (5-methoxyimidazo[1,2-a]quinolin-2-yl)-phenyl-methanone and its non-toxic, pharmaceutically acceptable acid addition salts.

20. A method of claim 15 selected from the group consisting of (5-isopropoxyimidazo[1,2-a]quinolin-2-yl)-phenyl-methanone and its non-toxic, pharmaceutically acceptable acid addition salts.

21. A method of claim 15 selected from the group consisting of (5-methylthioimidazo[1,2-a]quinolin-2-yl)-phenyl-methanone and its non-toxic, pharmaceutically acceptable acid addition salts.

* * * * *